US008846404B2

(12) United States Patent
Odom et al.

(10) Patent No.: US 8,846,404 B2
(45) Date of Patent: Sep. 30, 2014

(54) SYSTEM FOR VISUAL INDICATION OF MECHANICAL DAMAGE

(75) Inventors: Susan A. Odom, Champaign, IL (US); Mary M. Caruso, Urbana, IL (US); Aaron D. Finke, Urbana, IL (US); Aaron C. Jackson, Urbana, IL (US); Jeffrey S. Moore, Savoy, IL (US); Nancy R. Sottos, Champaign, IL (US); Scott R. White, Champaign, IL (US)

(73) Assignee: Board of Trustees of the University of Illinois, Urbana, IL (US)

( * ) Notice: Subject to any disclaimer, the term of this patent is extended or adjusted under 35 U.S.C. 154(b) by 493 days.

(21) Appl. No.: 13/168,166

(22) Filed: Jun. 24, 2011

(65) Prior Publication Data

US 2012/0196373 A1      Aug. 2, 2012

Related U.S. Application Data

(60) Provisional application No. 61/358,516, filed on Jun. 25, 2010.

(51) Int. Cl.
*G01N 31/22* (2006.01)
*G01N 21/78* (2006.01)
*B29C 73/22* (2006.01)

(52) U.S. Cl.
CPC ..................... *G01N 21/78* (2013.01)
USPC .................................. 436/2; 436/5

(58) Field of Classification Search
CPC ......... G01N 31/22; G01N 21/78; B29C 73/22
USPC ........................................................ 436/2, 5
See application file for complete search history.

(56) References Cited

U.S. PATENT DOCUMENTS 3,469,439 A      9/1969   Roberts et al.
5,561,173 A  *  10/1996   Dry .............................. 523/218
(Continued)

FOREIGN PATENT DOCUMENTS

WO         2010028057          3/2010

OTHER PUBLICATIONS

Eisler, B. et al, Journal of Polymer Science 1952, 8, 157-161.*
(Continued)

*Primary Examiner* — Arlen Soderquist
(74) *Attorney, Agent, or Firm* — Blanchard & Associates (57) ABSTRACT

A self-indicating material system may include a solid polymer matrix having a first color, a first plurality of capsules in the matrix, and a plurality of particles in the matrix. The first plurality of capsules includes a first reactant, and the plurality of particles includes a second reactant, which forms a product when in contact with the first reactant. When a crack forms in the polymer matrix, at least a portion of the first plurality of capsules is ruptured, the first and second reactants form the product in the matrix, and the portion of the polymer matrix containing the product has a second color different from the first color. A self-indicating material system may include a solid polymer matrix, a plurality of capsules in the matrix, and an activator in the matrix, where the polymer matrix includes a first polymer and has a first color, the plurality of capsules includes a polymerizer, and the activator is an activator for the polymerizer. When a crack forms in the polymer matrix, at least a portion of the plurality of capsules is ruptured, the polymerizer and the activator form a second polymer in the crack, and the second polymer has a second color different from the first color.

23 Claims, 6 Drawing Sheets

(56) References Cited

U.S. PATENT DOCUMENTS

| | | | |
|---|---|---|---|
| 5,660,624 A * | 8/1997 | Dry | 106/677 |
| 5,989,334 A * | 11/1999 | Dry | 106/677 |
| 6,075,072 A * | 6/2000 | Guilbert et al. | 523/200 |
| 6,261,360 B1 * | 7/2001 | Dry | 106/677 |
| 6,518,330 B2 * | 2/2003 | White et al. | 523/200 |
| 6,527,849 B2 * | 3/2003 | Dry | 106/677 |
| 6,858,659 B2 | 2/2005 | White et al. | |
| 7,022,179 B1 * | 4/2006 | Dry | 106/711 |
| 7,566,747 B2 | 7/2009 | Moore et al. | |
| 7,569,625 B2 * | 8/2009 | Keller et al. | 523/211 |
| 7,612,152 B2 * | 11/2009 | Braun et al. | 525/476 |
| 7,723,405 B2 * | 5/2010 | Braun et al. | 523/212 |
| 8,236,914 B2 | 8/2012 | Potisek et al. | |
| 8,383,697 B2 * | 2/2013 | Wilson et al. | 523/120 |
| 8,518,703 B1 * | 8/2013 | Wright | 436/5 |
| 8,529,846 B1 * | 9/2013 | Wright | 422/400 |
| 2001/0050032 A1 * | 12/2001 | Dry | 106/677 |
| 2006/0169180 A1 * | 8/2006 | Dry | 106/711 |
| 2006/0252852 A1 * | 11/2006 | Braun et al. | 523/200 |
| 2007/0166542 A1 * | 7/2007 | Braun et al. | 428/402.21 |
| 2007/0197383 A1 | 8/2007 | Koene et al. | |
| 2007/0282059 A1 * | 12/2007 | Keller et al. | 524/588 |
| 2008/0047472 A1 * | 2/2008 | Dry | 106/641 |
| 2008/0050612 A1 * | 2/2008 | Dry | 428/689 |
| 2008/0053338 A1 * | 3/2008 | Dry | 106/642 |
| 2008/0057296 A1 * | 3/2008 | Dry | 428/320.2 |
| 2008/0058445 A1 * | 3/2008 | Dry | 523/206 |
| 2008/0107888 A1 * | 5/2008 | Dry | 428/313.3 |
| 2008/0299391 A1 * | 12/2008 | White et al. | 428/402.21 |
| 2008/0305343 A1 * | 12/2008 | Toohey et al. | 428/447 |
| 2009/0015272 A1 * | 1/2009 | Jones et al. | 324/693 |
| 2009/0181254 A1 * | 7/2009 | White et al. | 428/402.2 |
| 2009/0191402 A1 | 7/2009 | Beiermann et al. | |
| 2009/0208684 A1 * | 8/2009 | Dunleavy et al. | 428/36.4 |
| 2010/0075134 A1 * | 3/2010 | Blaiszik et al. | 428/321.5 |
| 2010/0308276 A1 * | 12/2010 | Dry | 252/502 |
| 2010/0331445 A1 * | 12/2010 | Wilson et al. | 523/116 |
| 2011/0023611 A1 * | 2/2011 | Jones et al. | 73/629 |
| 2011/0039980 A1 * | 2/2011 | Caruso et al. | 523/400 |
| 2011/0272082 A1 * | 11/2011 | Dunleavy et al. | 156/94 |
| 2011/0287553 A1 * | 11/2011 | Hassan et al. | 436/164 |
| 2012/0067615 A1 | 3/2012 | Blaiszik et al. | |

OTHER PUBLICATIONS

Grubbs, R. H. et al, in "Materials for Nonlinear Optics" ACS Symposium Series 1991, chapter 45, pp. 672-682, Marder S. et al, Editor, American Chemical Society, Washington D.C.*
Jozefiak, T. H. et al, Journal of the American Chemical Society 1993, 115, 4705-4713.*
Schwab, P. et al, Journal of the American Chemical Society 1996, 118, 100-110.*
Pang, J. W. C. et al, Composites Science and Technology 2005, 65, 1791-1799.*
Wilson, G. O. et al, Chemistry of Materials 2008, 20, 3288-3297.*
Yuan, Y. C. et al, Macromolecules 2008, 41, 5197-5202.*
Liu, X. et al, Composites Science and Technology 2009, 69, 2102-2107.*
Patel, A, J, et al, Composites: Part A 2010, 41, 360-368.*
Capezzuto, et al., "A smart multifunctional polymer nanocomposites layer for the estimation of low-velocity impact damage in composite structures", "Composite Structures", 2010, pp. 1913-1919, vol. 92.
Chung, et al., "Crack Healing in Polymeric Materials via Photo-chemical [2+2] Cycloaddition", 2004, pp. 3982-3984, vol. 16.
Davis, et al., "Force-induced activation of covalent bonds in mechanoresponsive polymeric matericals", "Nature", May 7, 2009, pp. 6872, vol. 459.
Geiser, et al., "Conducting Organic Radical Cation Salts with Organic and Organometallic Anions", "Chem. Rev. ", 2004, pp. 5203-5241, vol. 104.
Kivala, et al., "Acetylene-Derived Strong Organic Acceptors for Planar and Nonplanar Push-Pull Chromophores", "Account of Chemical Research", 2009, pp. 235-248, vol. 42, No. 2.
Van Den Dungen, et al., "Use of a Profluorophore for Visualization of the Rupture of Capsules in Self-Healing Coatings", "Macromol. Rapid Commun. ", 2010, pp. 625-628, vol. 31.

* cited by examiner

| FIG. 6A | FIG. 6B | FIG. 6C | FIG. 6D |

| FIG. 7A | FIG. 7B | FIG. 7C |

SYSTEM FOR VISUAL INDICATION OF MECHANICAL DAMAGE

FEDERALLY SPONSORED RESEARCH OR DEVELOPMENT

The subject matter of this application may have been funded in part under a research grant from the Air Force Office of Scientific Research MURI under Grant Number FA9550-05-1-0346, and from the National Science Foundation ACC Fellowship under Grant Number 392 NSF CHF 09-36888 FLLW ARRA. The U.S. Government has certain rights in this invention.

REFERENCE TO RELATED APPLICATIONS

This application claims the benefit of U.S. Provisional Application No. 61/358,516 entitled "Microcapsule System For Visual Indication Of Mechanical Damage" filed Jun. 25, 2010, which is incorporated by reference in its entirety.

BACKGROUND

Damage in materials can be difficult to detect and almost impossible to repair. A successful method of autonomically repairing cracks that has the potential for significantly increasing the longevity of materials has been described, for example, in U.S. Pat. No. 6,518,330. This self-healing system includes a material containing, for example, solid particles of Grubbs catalyst and capsules containing liquid dicyclopentadiene (DCPD) embedded in an epoxy matrix. When a crack propagates through the material, it ruptures the microcapsules and releases DCPD into the crack plane. The DCPD then contacts the Grubbs catalyst, undergoes Ring Opening Metathesis Polymerization (ROMP), and cures to provide structural continuity where the crack had been.

Visual indication of damage detection is important in identifying damaged/stressed areas in polymers and composites used as structural supportive materials. Identifying damage can provide alert mechanisms to investigate the integrity of polymeric materials before catastrophic and/or irreversible system failure occurs.

SUMMARY

In one aspect, the invention provides a self-indicating material system that includes a solid polymer matrix having a first color, a first plurality of capsules in the matrix, and a plurality of particles in the matrix. The first plurality of capsules includes a first reactant, and the plurality of particles includes a second reactant. When a crack forms in the polymer matrix, at least a portion of the first plurality of capsules is ruptured, the first and second reactants form a product in the matrix, and the portion of the polymer matrix containing the product has a second color different from the first color.

In another aspect of the invention, there is a self-indicating material system that includes a solid polymer matrix including a first polymer and having a first color; a plurality of capsules in the matrix, the plurality of capsules including a polymerizer; and an activator for the polymerizer in the matrix. When a crack forms in the polymer matrix, at least a portion of the plurality of capsules is ruptured, the polymerizer and the activator form a second polymer in the crack, and the second polymer has a second color different from the first color.

In another aspect of the invention, there is a method of indicating mechanical damage in a solid polymer matrix that includes providing in the solid polymer matrix a first plurality of capsules and a plurality of particles. The solid polymer matrix has a first color, the first plurality of capsules includes a first reactant, and the plurality of particles includes a second reactant. When at least a portion of the first plurality of capsules is ruptured, the first reactant contacts the second reactant in the matrix, and a product is formed from the first and second reactants. The portion of the polymer matrix containing the product has a second color different from the first color.

In another aspect of the invention, there is a method of indicating mechanical damage in a solid polymer matrix that includes providing in the solid polymer matrix a plurality of capsules and an activator. The solid polymer matrix includes a first polymer and has a first color, the plurality of capsules includes a polymerizer, and the activator is an activator for the polymerizer. When at least a portion of the capsules is ruptured, the polymerizer contacts the activator in the matrix, and a second polymer is formed from the polymerizer and the activator. The second polymer has a second color different from the first color.

To provide a clear and more consistent understanding of the specification and claims of this application, the following definitions are provided.

The term "polymer" means a substance containing more than 100 repeat units. The term "polymer" includes soluble and/or fusible molecules having long chains of repeat units, and also includes insoluble and infusible networks. The term "prepolymer" means a substance containing less than 100 repeat units and that can undergo further reaction to form a polymer.

The term "matrix" means a continuous phase in a material.

The term "capsule" means a closed object having a capsule wall enclosing an interior volume that may contain a solid, liquid, gas, or combinations thereof, and having an aspect ratio of 1:1 to 1:10. The aspect ratio of an object is the ratio of the shortest axis to the longest axis, where these axes need not be perpendicular. A capsule may have any shape that falls within this aspect ratio, such as a sphere, a toroid, or an irregular ameboid shape. The surface of a capsule may have any texture, for example rough or smooth.

The term "polymerizer" means a composition that will form a polymer when it comes into contact with a corresponding activator for the polymerizer. Examples of polymerizers include monomers of polymers, such as styrene, ethylene, acrylates, methacrylates, and cyclic olefins such as dicyclopentadiene (DCPD) and cyclooctatetraene (COT); one or more monomers of a multi-monomer polymer system, such as diols, diamines and epoxides; prepolymers such as partially polymerized monomers still capable of further polymerization; and functionalized polymers capable of forming larger polymers or networks.

The term "activator" means anything that, when contacted or mixed with a polymerizer, will form a polymer. Examples of activators include catalysts and initiators. A corresponding activator for a polymerizer is an activator that, when contacted or mixed with that specific polymerizer, will form a polymer.

The term "catalyst" means a compound or moiety that will cause a polymerizable composition to polymerize, and that is not always consumed each time it causes polymerization. This is in contrast to initiators, which are always consumed at the time they cause polymerization. Examples of catalysts include ring opening metathesis polymerization (ROMP) catalysts such as Grubbs catalyst. Examples of catalysts also include silanol condensation catalysts such as titanates and dialkyltincarboxylates. A corresponding catalyst for a polymerizer is a catalyst that, when contacted or mixed with that specific polymerizer, will form a polymer.

The term "initiator" means a compound or moiety that will cause a polymerizable composition to polymerize and, in contrast to a catalyst, is always consumed at the time it causes polymerization. Examples of initiators include peroxides, which can form a radical to cause polymerization of an unsaturated monomer; a monomer of a multi-monomer polymer system, such as a diol, a diamine, and an epoxide; and amines, which can form a polymer with an epoxide. A corresponding initiator for a polymerizer is an initiator that, when contacted or mixed with that specific polymerizer, will form a polymer.

The term "solvent", in the context of a healing agent, means a liquid that can dissolve another substance, and that is not a polymerizer.

The term "encapsulant" means a material that will dissolve or swell in a polymerizer and, when combined with an activator, will protect the activator from reaction with materials used to form a solid polymer matrix. A corresponding encapsulant for a solid polymer matrix and for a polymerizer will protect an activator from reaction with materials used to form that specific solid polymer matrix and will dissolve or swell in that specific polymerizer.

The term "matrix precursor" means a composition that will form a polymer matrix when it is solidified. A matrix precursor may include a monomer and/or prepolymer that can polymerize to form a solid polymer matrix. A matrix precursor may include a polymer that is dissolved or dispersed in a solvent, and that can form a solid polymer matrix when the solvent is removed. A matrix precursor may include a polymer at a temperature above its melt temperature, and that can form a solid polymer matrix when cooled to a temperature below its melt temperature.

BRIEF DESCRIPTION OF THE DRAWINGS

The invention can be better understood with reference to the following drawings and description. The components in the figures are not necessarily to scale and are not intended to accurately represent molecules or their interactions, emphasis instead being placed upon illustrating the principles of the invention. Moreover, in the figures, like referenced numerals designate corresponding parts throughout the different views.

DETAILED DESCRIPTION

In accordance with the present invention a self-indicating material system includes a solid polymer matrix having a first color, a first plurality of capsules in the matrix, and a plurality of particles in the matrix. The first plurality of capsules includes a first reactant, and the plurality of particles includes a second reactant, which forms a product when in contact with the first reactant. When a crack forms in the polymer matrix, at least a portion of the first plurality of capsules is ruptured, the first and second reactants form the product in the matrix, and the portion of the polymer matrix containing the product has a second color different from the first color.

In accordance with the present invention a self-indicating material system includes a solid polymer matrix, a plurality of capsules in the matrix, and an activator in the matrix. The polymer matrix includes a first polymer and has a first color. The plurality of capsules includes a polymerizer, and the activator is an activator for the polymerizer. When a crack forms in the polymer matrix, at least a portion of the plurality of capsules is ruptured, the polymerizer and the activator form a second polymer in the crack, and the second polymer has a second color different from the first color.

Figure 1:
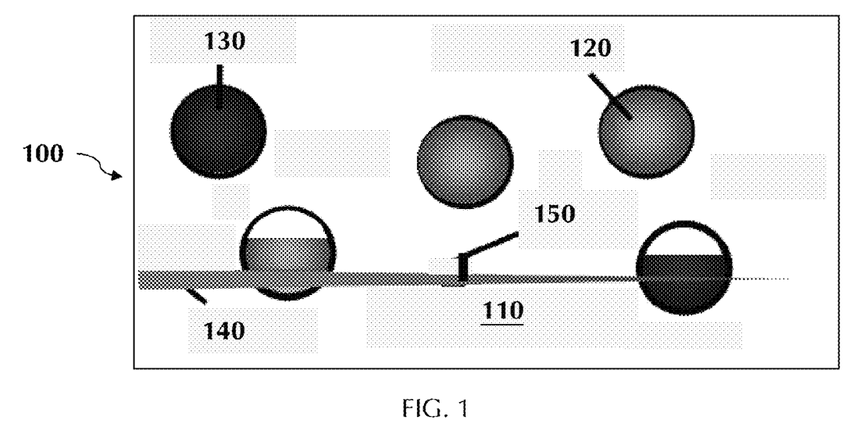
FIG. 1 depicts a schematic representation of a self-indicating material system.

FIG. 1 is a schematic representation of a material system 100 that includes a solid polymer matrix 110, a first plurality of capsules 120 containing a first reactant in the polymer matrix, and a plurality of particles 130 containing a second reactant in the polymer matrix. The solid polymer matrix 110 has a first color.

The solid polymer matrix 110 may include a polyamide such as nylon; a polyester such as poly(ethylene terephthalate) and polycaprolactone; a polycarbonate; a polyether; an epoxy polymer; an epoxy vinyl ester polymer; a polyimide such as polypyromellitimide (for example KAPTAN); a phenol-formaldehyde polymer such as BAKELITE; an amine-formaldehyde polymer such as a melamine polymer; a polysulfone; a poly(acrylonitrile-butadiene-styrene) (ABS); a polyurethane; a polyolefin such as polyethylene, polystyrene, polyacrylonitrile, a polyvinyl, polyvinyl chloride and poly(DCPD); a polyacrylate such as poly(ethyl acrylate); a poly(alkylacrylate) such as poly(methyl methacrylate); a polysilane such as poly(carborane-silane); and a polyphosphazene. The solid polymer matrix 110 may include an elastomer, such as an elastomeric polymer, an elastomeric copolymer, an elastomeric block copolymer, and an elastomeric polymer blend. Self-healing materials that include an elastomer as the solid polymer matrix are disclosed, for example, in U.S. Pat. No. 7,569,625 to Keller et al. The solid polymer matrix 110 may include a mixture of these polymers, including copolymers that include repeating units of two or more of these polymers, and/or including blends of two or more of these polymers.

The solid polymer matrix 110 may include other ingredients in addition to the polymeric material. For example, the matrix may contain one or more particulate fillers, reinforcing fibers, stabilizers, antioxidants, flame retardants, plasticizers, colorants and dyes, fragrances, or adhesion promoters. An adhesion promoter is a substance that increases the adhesion between two substances, such as the adhesion between two polymers. One type of adhesion promoter that may be present includes substances that promote adhesion between the solid polymer matrix 110 and the capsules 120, and/or between the solid polymer matrix 110 and the particles 130. The adhesion between the matrix and the capsules may influence whether the capsules will rupture or debond when a crack is formed in the matrix. To promote one or both of these forms of adhesion, various silane coupling agents may be used. Another type of adhesion promoter that may be present includes substances that promote adhesion between the solid polymer matrix 110 and a polymer that may be formed in the crack, such as a polymer formed from a polymerizer and activator present in the system 100. The adhesion between the matrix and this polymer may influence whether the material can be healed once damage has occurred. To promote the adhesion between the solid polymer matrix and the polymer formed in the crack, various unsaturated silane coupling agents may be used.

The solid polymer matrix 110 has a first color. Preferably the solid polymer matrix is not opaque, but rather is transparent or translucent. The solid polymer matrix may be transparent or translucent and may further have a color that provides a colored tinting to the material.

The first plurality of capsules 120 isolates the first reactant in the capsules until the material system 100 is subjected to damage that forms a crack in the polymer matrix 110. Once the damage occurs, the capsules in contact with the damaged area can rupture, releasing the first reactant into the crack plane.

The capsules 120 have an aspect ratio of from 1:1 to 1:10, preferably from 1:1 to 1:5, from 1:1 to 1:3, from 1:1 to 1:2, or from 1:1 to 1:1.5. In one example, the capsules may have an average diameter of from 10 nanometers (nm) to 1 millimeter (mm), more preferably from 30 to 500 micrometers, and more preferably from 50 to 300 micrometers. In another example, the capsules may have an average diameter less than 10 micrometers. Capsules having an average outer diameter less than 10 micrometers, and methods for making these capsules, are disclosed, for example, in U.S. Patent Application Publication 2008/0299391 with inventors White et al., published Dec. 4, 2008.

The capsules 120 have a capsule wall enclosing an interior volume containing a liquid. The thickness of the capsule wall may be, for example, from 30 nm to 10 micrometers. For capsules having an average diameter less than 10 micrometers, the thickness of the capsule wall may be from 30 nm to 150 nm, or from 50 nm to 90 nm. The selection of capsule wall thickness may depend on a variety of parameters, such as the nature of the solid polymer matrix, and the conditions for making and using the material. For example, a capsule wall that is too thick may not rupture when the interface with which it is in contact is damaged, while a capsules wall that is too thin may break during processing.

Capsules may be made by a variety of techniques, and from a variety of materials. Examples of materials from which the capsules may be made, and the techniques for making them include: polyurethane, formed by the reaction of isocyanates with a diol or triol; urea-formaldehyde (UF), formed by in situ polymerization; gelatin, formed by complex coacervation; polystyrene, formed by complex coacervation; polyurea, formed by the reaction of isocyanates with a diamine or a triamine, depending on the degree of crosslinking and brittleness desired; polystyrene or polydivinylbenzene formed by addition polymerization; and polyamide, formed by the use of a suitable acid chloride and a water soluble triamine. For capsules having an average diameter less than 10 micrometers, the capsule formation may include forming a microemulsion containing the capsule starting materials, and forming microcapsules from this microemulsion.

The capsules 120 may include a first reactant that is a donor or an acceptor of a charge-transfer substance. Examples of charge-transfer donors include tetrathiafulvalene (TTF), 4-dimethylaminophenylacetylene (DAP), bis(4-dimethylaminophenylacetylene) (BIS-DAP), bis(dimethylaminophenyl)acetylene (BAT), anisole, and derivatives thereof, including other alkynes that are connected to electron-donating groups. Examples of charge-transfer acceptors include tetracyanoquinodimethane (TCNQ), tetracyanoethylene (TCNE), quinones, and derivatives thereof.

The combination of a charge-transfer donor and a charge-transfer acceptor can form a charge-transfer substance having a color that is different from the colors of either the donor or the acceptor. The charge-transfer substance may be a charge-transfer salt, a charge-transfer molecule or a charge-transfer complex.

The capsules 120 may include a first reactant that is a polymerizer. For example the first reactant may include a monomer, a prepolymer, or a functionalized polymer having two or more reactive groups. For example, a polymerizer may include reactive groups such as alkene groups, epoxide groups, amine groups, phenol groups, aldehyde groups, hydroxyl groups, carboxylic acid groups, and/or isocyanate groups. Examples of polymerizers also include lactones (such as caprolactone) and lactams, which, when polymerized, will form polyesters and nylons, respectively.

The capsules 120 may include a first reactant that is an alkene-functionalized monomer, prepolymer or polymer, which may form a polymer when contacted with other alkene groups. Examples of alkene-functionalized polymerizers include monomers such as acrylates; alkylacrylates including methacrylates and ethacrylates; olefins including styrenes, isoprene and butadiene; and cyclic olefins including dicyclopentadiene (DCPD), norbornene, cyclooctadiene and cyclooctatetraene (COT). Preferably a polymerizer present as the first reactant can form a conjugated polymer. Examples of polymerizers that can form conjugated polymers include COT and its derivatives, including alkyl-substituted derivatives such as n-butyl-cyclooctatetraene (n-butylCOT).

The capsules 120 may include other ingredients in addition to the first reactant. For example, the capsules may contain one or more solvents, stabilizers, antioxidants, flame retardants, plasticizers, colorants and dyes, fragrances, or adhesion promoters. Examples of capsules that include a solvent are disclosed, for example, in copending U.S. patent application Ser. No. 12/739,537, with inventors Caruso et al., filed Apr. 23, 2010. The capsules may include an aprotic solvent, a protic solvent, or a mixture of these. Examples of aprotic solvents include hydrocarbons, such as cyclohexane; aromatic hydrocarbons, such as toluene and xylenes; halogenated hydrocarbons, such as dichloromethane; halogenated aromatic hydrocarbons, such as chlorobenzene and dichlorobenzene; substituted aromatic solvents, such as nitrobenzene; ethers, such as tetrahydrofuran (THF) and dioxane; ketones, such as acetone and methyl ethyl ketone; esters, such as ethyl acetate, hexyl acetate, ethyl phenylacetate (EPA) and phenylacetate (PA); tertiary amides, such as dimethyl acetamide (DMA), dimethyl formamide (DMF) and N-methylpyrrolidine (NMP); nitriles, such as acetonitrile; and sulfoxides, such as dimethyl sulfoxide (DMSO). Examples of protic solvents include water; alcohols, such as ethanol, isopropanol, butanol, cyclohexanol, and glycols; and primary and secondary amides, such as acetamide and formamide.

The plurality of particles 130 includes a second reactant, which forms a product with the first reactant. When the first reactant in capsules 120 is a donor or an acceptor of a charge-transfer substance, the particles 130 preferably include a second reactant that is complementary to an acceptor or a donor of the charge-transfer substance. The combination of a charge-transfer donor and a charge-transfer acceptor can form a charge-transfer substance having a color that is different from the colors of either the donor or the acceptor. The charge-transfer substance may be a charge-transfer salt, a charge-transfer molecule or a charge-transfer complex.

If the first reactant in capsules 120 is a charge-transfer donor, the second reactant in the particles 130 preferably is a corresponding charge-transfer acceptor, which forms a charge-transfer substance with the first reactant. Likewise, if the first reactant is a charge-transfer acceptor, the second reactant preferably is a corresponding charge-transfer donor, which forms a charge-transfer substance with the first reactant. Examples of charge-transfer donors include TTF, DAP, BAT, BIS-DAP, anisole, and derivatives thereof. Examples of charge-transfer acceptors include TCNQ, TCNE, quinones, and derivatives thereof.

Figure 2:
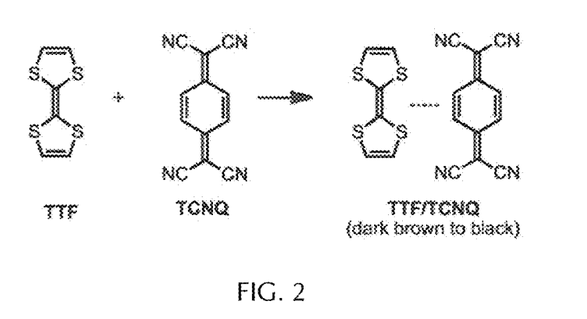
FIG. 2 illustrates a reaction scheme for an example in which the first reactant is the charge-transfer donor tetrathiafulvalene (TTF), and the second reactant is charge-transfer acceptor tetracyanoquinodimethane (TCNQ). The product of the first and second reactants is a charge-transfer salt.

FIG. 2 illustrates a reaction scheme for an example in which the first reactant is the charge-transfer donor TTF, and the second reactant is charge-transfer acceptor TCNQ. The product of the first and second reactants is a charge-transfer salt.

Figure 3:
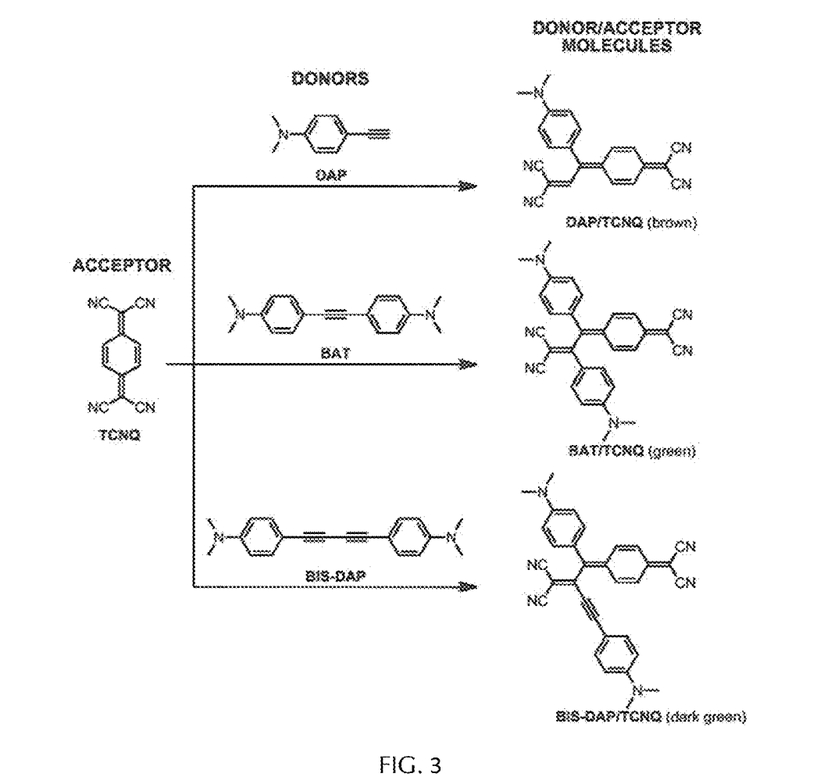
FIG. 3 illustrates a reaction scheme for an example in which the first reactant is a charge-transfer donor 4-dimethylaminophenylacetylene (DAP), bis(4-dimethylaminophenylacetylene) (BIS-DAP) or bis(dimethylaminophenyl)acetylene (BAT), and the second reactant is charge-transfer acceptor TCNQ. The product of the first and second reactants is a charge-transfer compound.

FIG. 3 illustrates a reaction scheme for an example in which the first reactant is a charge-transfer donor DAP, BAT or BIS-DAP, and the second reactant is charge-transfer acceptor TCNQ. The product of the first and second reactants is a charge-transfer compound.

Figure 4:
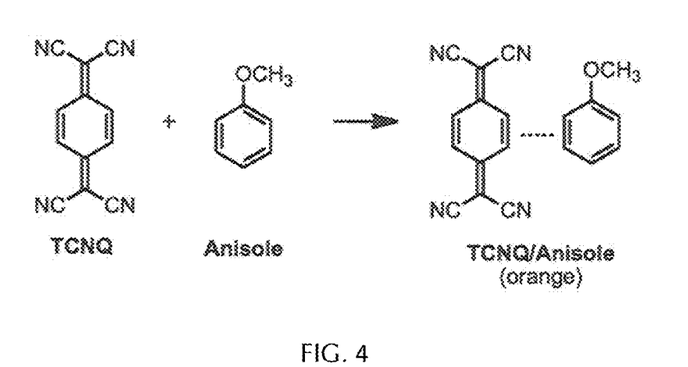
FIG. 4 illustrates a reaction scheme for an example in which the first reactant is the charge-transfer donor anisole, and the second reactant is charge-transfer acceptor TCNQ. The product of the first and second reactants is a charge-transfer complex.

FIG. 4 illustrates a reaction scheme for an example in which the first reactant is the charge-transfer donor anisole, and the second reactant is charge-transfer acceptor TCNQ. The product of the first and second reactants is a charge-transfer complex.

When the first reactant in capsules 120 is a polymerizer, the solid polymer matrix 110 preferably includes an activator for the polymerizer. Examples of activators include corresponding catalysts for polymerizable cyclic olefins, including ring opening metathesis polymerization (ROMP) catalysts such as Schrock catalysts and Grubbs catalysts, including the $2_{nd}$-generation Grubbs catalyst and the Grubbs-Love catalyst. Examples of activators include corresponding catalysts for lactones and lactams, including cyclic ester polymerization catalysts and cyclic amide polymerization catalysts such as scandium triflate.

If the first reactant in capsules 120 is a polymerizer, the particles 130 may be particles of the pure activator, they may be a mixture of the activator and an encapsulant, or they may be a second plurality of capsules containing the activator. The particles 130 also may be absent from the matrix, and the activator may be present as a free, non-particulate substance in the polymer matrix or bonded to the polymer matrix.

The particles 130 may include a pure second reactant in solid form, such as crystals of an activator or of a charge-transfer acceptor or donor. These activator particles preferably are microparticles having an average diameter of at most 500 micrometers. Specific examples of pure reactants in solid form include solid particles of Grubbs catalyst or of Grubbs-Love catalyst.

The particles 130 may include a mixture of a second reactant and an encapsulant. These particles may be made by a variety of techniques, and from a variety of materials. For example, small particles or a powder of the second reactant may be dispersed into a liquid containing the encapsulant, followed by solidification of the mixture of encapsulant and reactant. These particles preferably are microparticles having an average diameter of at most 500 micrometers. The encapsulant preferably is soluble in, or swells in, the contents of the capsules 120, and is a solid at room temperature. The contents of the capsules 120 may dissolve the encapsulant, releasing the second reactant and forming the product. The contents of the capsules 120 may swell the encapsulant so that the particle can be penetrated by the first reactant sufficiently to allow reaction with the second reactant. Examples of particles that include an activator and an encapsulant are disclosed, for example, in U.S. Pat. No. 7,566,747 to Moore et al.

The particles 130 may include capsules, and a liquid that includes the second reactant in the capsules. This second plurality of capsules may be as described above for the first plurality of capsules, and may include other ingredients in addition to the activator. For example, the second plurality of capsules may contain one or more stabilizers, antioxidants, flame retardants, plasticizers, colorants and dyes, fragrances, or adhesion promoters.

Referring to FIG. 1, when a crack 140 forms in the polymer matrix, at least a portion of the first plurality of capsules 120 is ruptured, and the first and second reactants form a product 150 in the matrix. The portion of the polymer matrix 110 containing the product 150 has a second color different from the first color. The solid polymer matrix 110 may be a continuous phase of a coating, and the crack 140 may be a scratch or an abrasion at the surface of the polymer matrix.

The product 150 may be opaque, transparent or translucent. The product may be transparent or translucent and may further have a color that provides a colored tinting to the product. Preferably the product 150 can be observed visually through the solid polymer matrix 110.

The first reactant is released into the crack plane upon rupturing of the first plurality of capsules 120. The first reactant may react with the second reactant upon contact of the first reactant with particles 130. The first reactant may dissolve an encapsulant that is present in the particles 130 prior to and/or during the reaction between the first and second reactants. If the particles 130 are a second plurality of capsules, the second plurality of capsules may rupture when the crack 140 forms in the polymer matrix, releasing the second reactant into the crack plane.

In one example, when the first and second reactants are a complementary charge-transfer donor/acceptor pair, a charge-transfer salt formed from the donor and acceptor can provide for electrical conductivity in the crack. This may be advantageous for material systems that include electrical circuit components, as the charge-transfer salt may restore an electrical connection that is initially broken by the crack in the polymer matrix. The color of the charge-transfer salt may provide identification of the mechanical damage sustained by the polymer matrix, in addition to restoring the electrical connection.

In another example, when the first reactant is a polymerizer and the second reactant is an activator for the polymerizer, a polymer formed from the polymerizer and the activator may provide for structural continuity in the crack. This may provide advantageous autonomic self-healing to the material system. The color of the polymer product may provide identification of the mechanical damage sustained by the polymer matrix, in addition to restoring the mechanical properties of the material.

A method of making a self-indicating material system, such as material system 100, may include combining ingredients including a matrix precursor, a first plurality of capsules, and a plurality of particles. The method further includes solidifying the matrix precursor to form a solid polymer matrix. The first plurality of capsules includes a first reactant, and the plurality of particles includes a second reactant. The method may further include forming the first plurality of capsules and/or the plurality of particles. The matrix precursor may be any substance that can form a solid polymer matrix when solidified.

A method of making a self-indicating material system, such as material system 100, may include combining ingredients including a matrix precursor, a plurality of capsules, and an activator for a polymerizer. The method further includes solidifying the matrix precursor to form a solid polymer matrix. The plurality of capsules includes a polymerizer, and the activator is an activator for the polymerizer. The method may further include forming the plurality of capsules. The matrix precursor may be any substance that can form a solid polymer matrix when solidified.

In one example, the matrix precursor includes a monomer and/or prepolymer that can polymerize to form a polymer. The capsules, particles and/or activator may be mixed with the monomer or prepolymer. The matrix precursor may then be solidified by polymerizing the monomer and/or prepolymer of the matrix precursor to form the solid polymer matrix.

In another example, the matrix precursor includes a polymer in a matrix solvent. The polymer may be dissolved or dispersed in the matrix solvent to form the matrix precursor, and the capsules, particles and/or activator then mixed into the matrix precursor. The matrix precursor may be solidified by removing at least a portion of the matrix solvent from the composition to form the solid polymer matrix.

In another example, the matrix precursor includes a polymer that is at a temperature above its melting temperature. The polymer may be melted to form the matrix precursor and then mixed with the capsules, particles and/or activator. The matrix precursor may be solidified by cooling the composition to a temperature below the melt temperature of the polymer to form the solid polymer matrix.

The following examples are provided to illustrate one or more preferred embodiments of the invention. Numerous variations can be made to the following examples that lie within the scope of the invention.

EXAMPLES

Materials and Methods

Urea, resorcinol, formalin, 3-bromopyridine, and the Grubbs $2^{nd}$ generation catalyst were purchased from Aldrich Chemical Co. Ethylene-maleic anhydride copolymer (Zemac-400) powder with an average molecular weight of 400 kDa (Vertellus) was used as a 2.5 wt % aqueous solution. Polyacrylic acid (PAA), 25 wt. % in water, with an average molecular weight of 50 kDa, was purchased from Polysciences. The commercial polyurethane prepolymer, Desmodur® L 75, was purchased from Bayer Material Science and was used as received. 1,3,5,7-Cyclooctatetraene (COT) was purchased from Equinox Chemicals, LLC. The Grubbs-Love catalyst was synthesized according to Love et al. (J. A. Love, J. P. Morgan, T. M. Trnka, R. H. Grubbs, *Angew. Chem. Int. Ed.* 2002, 41, 4035).

Optical micrographs of dried, sieved capsules in mineral oil on glass slides were taken using a Leica DMR Optical Microscope. Images of dried capsules were obtained using SEM (FEI/Philips XL30 ESEM-FEG) after sputter coating with a gold-palladium source. Thermogravimetric analysis (TGA) was performed on a Mettler-Toledo TGA851$^e$, calibrated by indium, aluminum, and zinc standards. For dynamic TGA scans, a heating rate of 10° C.·min$^{-1}$ was used. For isothermal TGA, samples were heated from 25-180° C. at 10° C.·min$^{-1}$, held at 180° C. for 2 h, then heated from 180-400° C. at 10° C.·min$^{-1}$. Experiments were performed under nitrogen atmosphere. For each TGA experiment, 5-10 mg of accurately weighed sample was used.

Example 1

Formation of Capsules Containing a Charge-Transfer Donor or Acceptor

A 600 mL beaker containing 100 mL of deionized water and 25 mL of 2.5% (wt/vol) ethylene co-maleic anhydride solution was placed in a temperature controlled water bath equipped with a mechanical stirring blade (40 mm diameter) and brought to 400 rpm. To this aqueous solution was added the ingredients for forming a capsule wall: urea (2.50 g), ammonium chloride (0.25 g), and resorcinol (0.25 g). The pH was then adjusted from 2.7 to 3.5 by addition of aqueous NaOH solution. To this stirred solution was then added a mixture of either a charge-transfer donor or a charge-transfer acceptor. The charge-transfer donor mixture included phenyl acetate (PA) solvent and either tetrathiafulvalene (TTF), 4-dimethylaminophenylacetylene (DAP), bis(4-dimethylaminophenylacetylene) (BIS-DAP) or bis(dimethylaminophenyl)acetylene (BAT); or the charge-transfer donor mixture included anisole without PA. The charge-transfer acceptor mixture included tetracyanoquinodimethane (TCNQ), in PA. Each mixture was sonicated at 40° C. for 30 min to ensure dissolution of the solids. Addition of a charge-transfer donor/acceptor mixture formed an emulsion in the beaker. After 10 min, 6.33 g of formalin solution was added, and the temperature was increased to 55° C. at 10° C./min. The reaction proceeded under continuous stirring for 4 h, after which the reaction mixture was allowed to cool to room temperature. The reaction mixture was filtered the next day, and the isolated capsules were washed with water, dried under air for at least 6 h, and then purified by sieving.

Figure 5A:
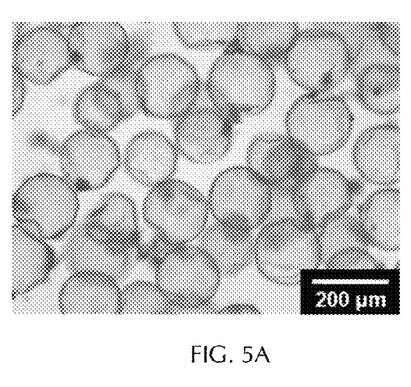
FIGS. 5A and 5B depict optical microscopy images of capsules containing a charge-transfer donor (5A) or a charge-transfer acceptor (5B).
Figure 5B:
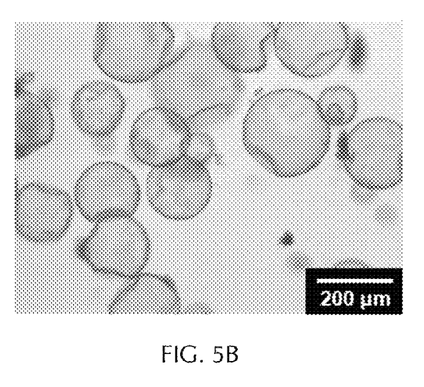

FIG. 5A depicts an optical microscopy image of the poly (urea-formaldehyde) capsules containing the charge-transfer donor TTF in PA. FIG. 5B depicts an optical microscopy image of the poly(urea-formaldehyde) capsules containing the charge-transfer acceptor TCNQ in PA.

Example 2

Formation of Charge-Transfer Salt from Rupture of Capsules Containing a Charge-Transfer Donor and Capsules Containing a Charge-Transfer Acceptor Two types of capsules formed in Example 1-50 mg capsules containing the charge-transfer donor TTF in PA and 50 mg capsules containing the charge-transfer acceptor TCNQ in PA—were pressed between glass slides to rupture the capsules. Capsules similar to those formed in Example 1, but including only PA without any donor or acceptor, also were ruptured between glass slides. In addition, a 1:1 by weight mixture of the capsules containing TTF in phenyl acetate and the capsules containing TCNQ in phenyl acetate were pressed between glass slides to rupture the capsules.

The mixture resulting from the combined capsules was a dark brown/black color, which was distinct from the colors observed from the other ruptured capsules. The color of the combined capsules after rupture depended on the concentrations of the donor and the acceptor in each set of capsules, and also depended on the time between the capsule rupture and the color observation. An increase in the donor/acceptor concentration and/or an increase in the time between the capsule rupture and the color observation correlate with a darker observed color of the combined capsules after rupture. The presence of a TTF-TCNQ charge-transfer salt in the mixture resulting from crushing the combined capsules was confirmed by optical microscopy, infrared (IR) spectroscopy and x-ray diffraction.

Figure 6A:
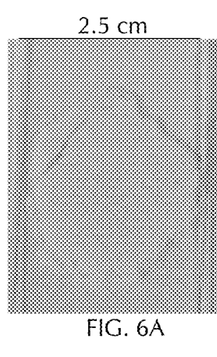
FIGS. 6A-6D depict optical microscopy images of ruptured capsules containing only phenyl acetate (6A), ruptured capsules containing the charge-transfer donor TTF (6B), ruptured capsules containing the charge-transfer acceptor TCNQ in phenyl acetate (6C), and a combination of ruptured capsules containing TTF and ruptured capsules containing TCNQ in phenyl acetate (6D).
Figure 6B:
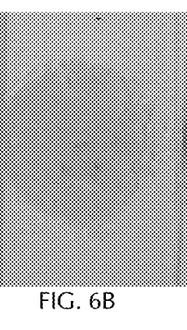
Figure 6C:
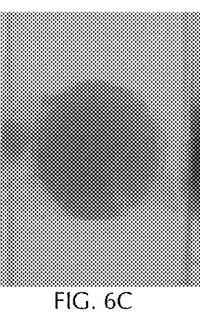
Figure 6D:
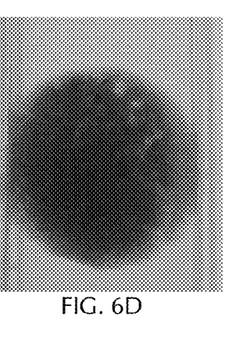

FIG. 6A depicts an optical microscopy image of capsules containing only phenyl acetate. FIG. 6B depicts an optical microscopy image of the capsules containing TTF in phenyl acetate. FIG. 6C depicts an optical microscopy image of the capsules containing TCNQ in phenyl acetate. FIG. 6D depicts an optical microscopy image of a 1:1 by weight mixture of the capsules containing TTF in phenyl acetate and the capsules containing TCNQ in phenyl acetate.

Example 3

Formation of Charge-Transfer Molecule from Rupture of Capsules Containing a Charge-Transfer Donor and Capsules Containing a Charge-Transfer Acceptor The two types of capsules formed in Example 1—capsules containing one of the charge-transfer donors DAP, BAT or BIS-DAP in PA, and capsules containing the charge-transfer acceptor TCNQ in PA—were pressed between glass slides to rupture the capsules. As in Example 2, donor capsules and acceptor capsules also were combined and pressed between glass slides to rupture the capsules. The colors observed for the ruptured capsules, whether alone or in combination, were confirmed by UV-Vis spectroscopy of the individual and combined charge-transfer donors and acceptors.

Figure 7A:
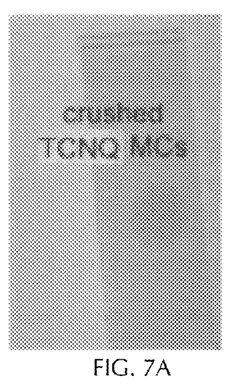
FIGS. 7A-7C depict optical microscopy images of ruptured capsules containing the charge-transfer acceptor TCNQ in phenyl acetate (7A), ruptured capsules containing the charge-transfer donor DAP (7B), and a combination of ruptured capsules containing DAP and ruptured capsules containing TCNQ in phenyl acetate (7C).
Figure 7B:
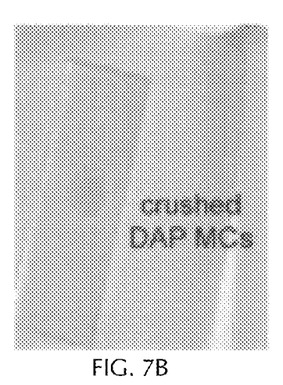
Figure 7C:
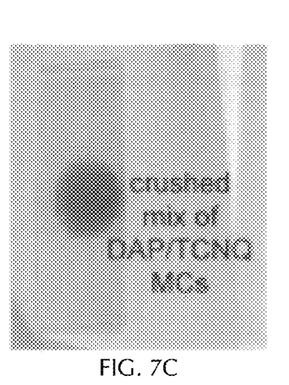

FIG. 7A depicts an optical microscopy image of the capsules containing TCNQ in phenyl acetate. FIG. 7B depicts an optical microscopy image of the capsules containing DAP in phenyl acetate. FIG. 7C depicts an optical microscopy image of a mixture of the capsules containing DAP in phenyl acetate and the capsules containing TCNQ in phenyl acetate. The mixture resulting from the combined capsules was a dark brown color, which was distinct from the yellow color of the ruptured TCNQ capsules and the colorless ruptured DAP capsules.

Figure 8A:
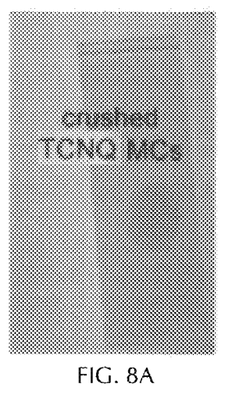
FIGS. 8A-8C depict optical microscopy images of ruptured capsules containing the charge-transfer acceptor TCNQ in phenyl acetate (8A), ruptured capsules containing the charge-transfer donor BIS-DAP (8B), and a combination of ruptured capsules containing BIS-DAP and ruptured capsules containing TCNQ in phenyl acetate (8C).
Figure 8B:
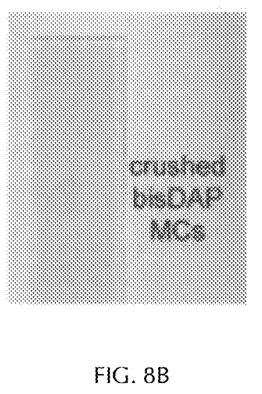
Figure 8C:
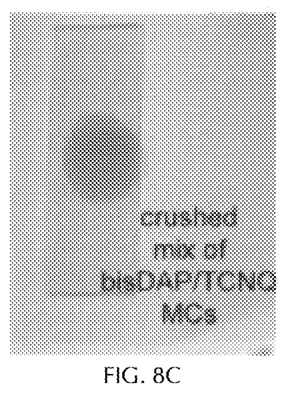

FIG. 8A depicts an optical microscopy image of the capsules containing TCNQ in phenyl acetate. FIG. 8B depicts an optical microscopy image of the capsules containing BIS-DAP in phenyl acetate. FIG. 8C depicts an optical microscopy image of a mixture of the capsules containing BIS-DAP in phenyl acetate and the capsules containing TCNQ in phenyl acetate. The mixture resulting from the combined capsules was a dark green color, which was distinct from the yellow color of the ruptured TCNQ capsules and the colorless ruptured BIS-DAP capsules.

Figure 9A:
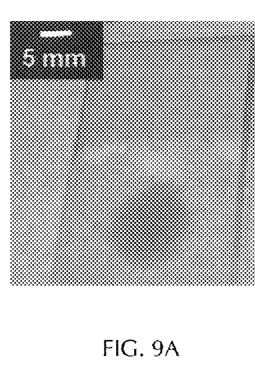
FIGS. 9A-9C depict optical microscopy images of ruptured capsules containing the charge-transfer acceptor TCNQ in phenyl acetate (9A), ruptured capsules containing the charge-transfer donor BAT (9B), and a combination of ruptured capsules containing BAT and ruptured capsules containing TCNQ in phenyl acetate (9C).
Figure 9B:
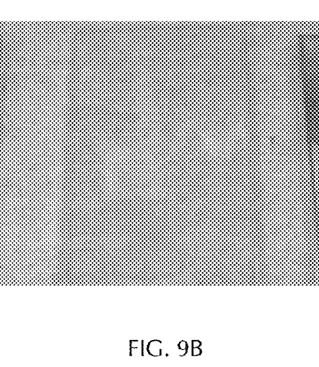
Figure 9C:
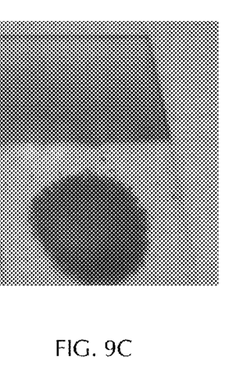

FIG. 9A depicts an optical microscopy image of the capsules containing TCNQ in phenyl acetate. FIG. 9B depicts an optical microscopy image of the capsules containing BAT in phenyl acetate. FIG. 9C depicts an optical microscopy image of a mixture of the capsules containing BAT in phenyl acetate and the capsules containing TCNQ in phenyl acetate. The mixture resulting from the combined capsules was a green color, which was distinct from the yellow color of the ruptured TCNQ capsules and the colorless ruptured BAT capsules.

Example 4

Formation of Charge-Transfer Complex from Rupture of Capsules Containing a Charge-Transfer Donor and Capsules Containing a Charge-Transfer Acceptor The two types of capsules formed in Example 1—capsules containing the charge-transfer donor anisole, and capsules containing the charge-transfer acceptor TCNQ in PA—were pressed between glass slides to rupture the capsules. As in Example 2, donor capsules and acceptor capsules also were combined and pressed between glass slides to rupture the capsules.

Figure 10A:
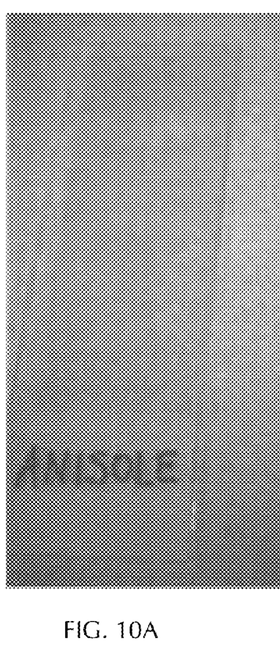
FIGS. 10A-10C depict optical microscopy images of ruptured capsules containing the charge-transfer donor anisole (10A), ruptured capsules containing the charge-transfer acceptor TCNQ in phenyl acetate (10B), and a combination of ruptured capsules containing anisole and ruptured capsules containing TCNQ in phenyl acetate (10C).
Figure 10B:
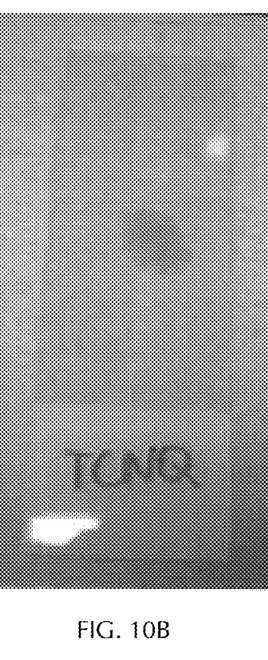
Figure 10C:
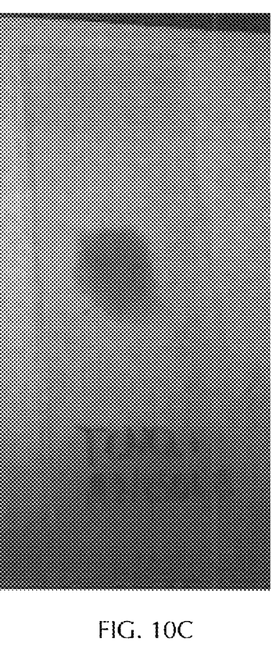

FIG. 10A depicts an optical microscopy image of the capsules containing anisole. FIG. 10B depicts an optical microscopy image of the capsules containing TCNQ in phenyl acetate. FIG. 10C depicts an optical microscopy image of a mixture of the capsules containing anisole and the capsules containing TCNQ in phenyl acetate. The mixture resulting from the combined capsules was a bright orange color, which was distinct from the yellow color of the ruptured TCNQ capsules and the colorless ruptured anisole capsules.

Example 5

Formation of Capsules Containing a Polymerizer

Capsules containing cyclooctatetraene (COT) were prepared according to the procedures of Example 1, except that the capsule shell wall was thickened by adding a polyurethane prepolymer to the COT prior to adding the COT solution to the reaction. The addition of the polyurethane prepolymer was believed to improve stability of the capsules and to decrease leaching of the COT from the capsules. Thermogravimetric analysis (TGA) showed no weight loss from the capsules containing COT until the temperature was 150° C., just above the 142° C. boiling point of COT. $^1$H NMR spectroscopy of capsules after rupturing and filtering the resulting liquid confirmed that COT was present in the capsules, having undergone negligible degradation.

Example 6

Formation of Particles Containing an Activator for COT

Particles containing an activator for COT were formed by combining the activator with an encapsulant. In ambient conditions, paraffin wax and Grubbs-Love Catalyst were combined in a vial. A solution of water, poly(ethylene-co-maleic anhydride) and octanol was placed in a beaker, placed in an 82° C. water bath, and stirred with a mechanical stirrer at 900 RPM. The vial containing the wax and the catalyst was submerged in the same 82° C. water bath. After 10 min, the wax had melted and the aqueous solution had reached 65-70° C. The vial with the molten wax was shaken to disperse the catalyst. The vial was then opened (in air), and the wax was poured into the aqueous solution. After 2 min, water at 0° C. was quickly added, and the stirring was stopped. The particles were collected by filtration and dried under vacuum.

Example 7

Figure 11A:
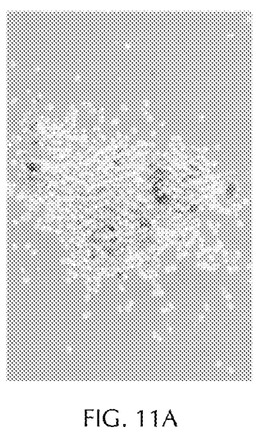
FIGS. 11A-11C depict optical microscopy images of a mixture of capsules containing a cyclooctatetraene (COT) polymerizer and particles containing an activator for the COT polymerizer before rupturing of the capsules (11A), 1 minute after the rupture of the capsules (11B), and 30 minutes after the rupture of the capsules (11C).
Figure 11B:
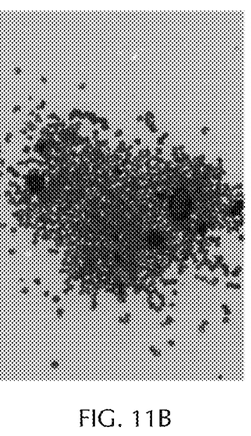
Figure 11C:
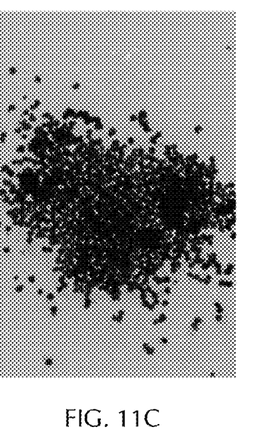

Formation of Conjugated Polymer from Rupture of Capsules Containing a Polymerizer and an Activator for the Polymerizer The capsules formed in Example 5 were combined with the particles formed in Example 6 and were imaged by optical microscopy. The capsule/particle mixture was then pressed between glass slides to rupture the capsules. The mixture resulting from the rupture of the capsules in the presence of the particles was initially a bright red color, which was distinct from the speckled yellow color of the mixture prior to capsule rupture. This mixture then became a dark purple color over the next 30 minutes. The observed colors are consistent with the formation of polyacetylene from the COT and the catalyst, as depicted in the reaction scheme below:

where n is an integer, and "Ru cat" represents a Grubbs-Love catalyst having the structure:

FIG. 11A depicts an optical microscopy image of the capsule/particle mixture before the capsules were ruptured. FIG. 11B depicts an optical microscopy image of the mixture 1 minute after the capsules were ruptured. FIG. 11C depicts an optical microscopy image of the mixture 30 minutes after the capsules were ruptured.

Example 8

Formation of a Self-Indicating Material System

Capsules containing COT according to Example 5 and particles containing Grubbs-Love catalyst according to Example 6 were incorporated into poly(acrylic acid) (PAA) films. To prepare the PAA films, 0.037 g COT capsules and 0.004 g catalyst particles were mixed into 1 mL of a solution of PAA. The solution was placed under vacuum for 5 minutes to remove air bubbles, and was then deposited on glass slides at 0.3 mL per square inch of slide. The slide was exposed to a continuous flow of dry air for 24 hours to remove water. The films contained 13 wt % COT capsules and 1.3 wt % Grubbs-Love catalyst particles, and had a thickness of approximately 500 micrometers. Control PAA films were prepared in which (a) only COT capsules were incorporated, (b) only catalyst particles were incorporated, or (c) neither catalyst particles nor COT capsules were incorporated.

After the films had cured overnight at room temperature, the films were scratched with a razor blade. Within 5 minutes of the scratch damage, the scratched region of the PAA films containing both COT capsules and catalyst particles displayed a red-orange color, consistent with the color change observed when crushing capsules and catalyst together in Example 7. Within 30 minutes of the scratch damage, the color at the scratched area in these PAA films turned a dark purple color. In all cases, the control PAA films did not show any color change at the scratched area.

Figure 12:
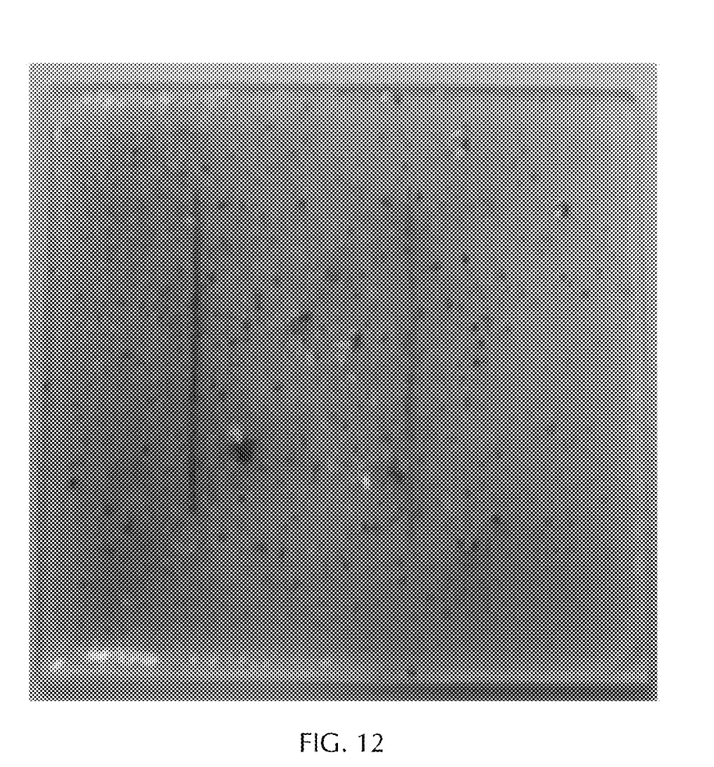
FIG. 12 depicts an optical image of a PAA film containing capsules containing a COT polymerizer and particles containing an activator for the COT polymerizer, where the film has been scratched 2 hours prior to the image (left) and 5 minutes prior to the image (right).
Figure 13:
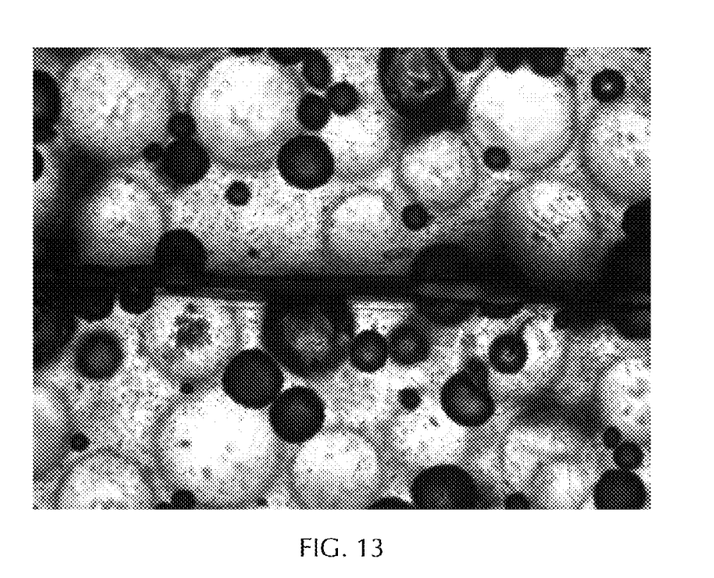
FIG. 13 depicts an optical microscopy image of PAA film containing capsules containing a COT polymerizer and particles containing an activator for the COT polymerizer, where the film has been scratched 5 minutes prior to the image.

FIG. 12 depicts an optical image of a PAA film containing COT capsules and catalyst particles. The scratch on the left corresponds to a scratch formed 2 hours prior to obtaining the image, and the scratch on the right corresponds to a scratch formed 5 minutes prior to the image. FIG. 13 depicts an optical microscopy image of a scratched area of a PAA film containing COT capsules and catalyst particles, obtained 5 minutes after formation of the scratch.

While various embodiments of the invention have been described, it will be apparent to those of ordinary skill in the art that other embodiments and implementations are possible within the scope of the invention. Accordingly, the invention is not to be restricted except in light of the attached claims and their equivalents.

What is claimed is:

1. A self-indicating material system, comprising:
a solid polymer matrix having a first color;
a first plurality of capsules in the matrix, the first plurality of capsules comprising a first reactant; and
a plurality of particles in the matrix, the plurality of particles comprising a second reactant;
where, when a crack forms in the polymer matrix, at least a portion of the first plurality of capsules is ruptured, the first and second reactants form a product in the matrix, and the portion of the polymer matrix containing the product has a second color different from the first color,
where the first reactant is a charge-transfer donor, the second reactant is a charge-transfer acceptor, and the product is a charge-transfer substance.

2. The system of claim 1, where the plurality of particles comprises the second reactant and an encapsulant.

3. The system of claim 1, where the plurality of particles comprises a second plurality of capsules; and at least a portion of the second plurality of capsules is ruptured when the crack forms in the polymer matrix.

4. The system of claim 3, where the second plurality of capsules further comprises a solvent.

5. The system of claim 1, where the first reactant comprises TTF, the second reactant comprises TCNQ, and the product comprises a charge-transfer salt.

6. The system of claim 5, where the crack breaks an electrical connection within the polymer matrix, and
the charge-transfer salt restores the electrical connection.

7. The system of claim 1, where
the first reactant comprises a charge-transfer donor selected from the group consisting of DAP, BIS-DAP and BAT,
the second reactant comprises TCNQ, and
the product comprises a charge-transfer molecule.

8. The system of claim 1, where the first reactant comprises anisole, the second reactant comprises TCNQ, and the product comprises a charge-transfer complex.

9. A self-indicating material system, comprising:
a solid polymer matrix comprising a first polymer and having a first color;
a plurality of capsules in the matrix, the plurality of capsules comprising a polymerizer; and
an activator for the polymerizer in the matrix;
where, when a crack forms in the polymer matrix, at least a portion of the plurality of capsules is ruptured, the polymerizer and the activator form a second polymer in the crack, and the second polymer has a second color different from the first color, and
where the activator comprises a metathesis catalyst and the second polymer comprises conjugated carbon-carbon double bonds.

10. The system of claim 9, where the activator is present with an encapsulant as a plurality of particles.

11. The system of claim 9, where the polymerizer comprises cyclooctatetraene, and the product comprises poly(acetylene).

12. The system of claim 9, where the metathesis catalyst comprises the Grubbs-Love catalyst.

13. The system of claim 9, where the material system further is a self-healing material system.

14. A method of indicating mechanical damage in a solid polymer matrix, comprising:
providing in the solid polymer matrix a first plurality of capsules and a plurality of particles;
where the solid polymer matrix has a first color,
the first plurality of capsules comprises a first reactant, and the plurality of particles comprises a second reactant;
where, when at least a portion of the first plurality of capsules is ruptured, the first reactant contacts the second reactant in the matrix, and a product is formed from the first and second reactants; and
the portion of the polymer matrix containing the product has a second color different from the first color,
where the first reactant is a charge-transfer donor, the second reactant is a charge-transfer acceptor, and the product is a charge-transfer substance.

15. A method of indicating mechanical damage in a solid polymer matrix, comprising:
providing in the solid polymer matrix a plurality of capsules and an activator;
where the solid polymer matrix comprises a first polymer and has a first color,
the plurality of capsules comprises a polymerizer, and the activator is an activator for the polymerizer;
where, when at least a portion of the capsules is ruptured, the polymerizer contacts the activator in the matrix, and a second polymer is formed from the polymerizer and the activator; and
the second polymer has a second color different from the first color, and
where the activator comprises a metathesis catalyst and the second polymer comprises conjugated carbon-carbon double bonds.

16. A self-indicating material system, comprising:
a solid polymer matrix having a first color;
a first plurality of capsules in the matrix, the first plurality of capsules comprising a first reactant; and
a plurality of particles in the matrix, the plurality of particles comprising a second reactant;
where, when a crack forms in the polymer matrix, at least a portion of the first plurality of capsules is ruptured, the first and second reactants form a product in the matrix, and the portion of the polymer matrix containing the product has a second color different from the first color, and
where the activator comprises a metathesis catalyst and the second polymer comprises conjugated carbon-carbon double bonds.

17. The system of claim 16, where the plurality of particles comprises the second reactant and an encapsulant.

18. The system of claim 16, where the plurality of particles comprises a second plurality of capsules; and at least a portion of the second plurality of capsules is ruptured when the crack forms in the polymer matrix.

19. The system of claim 18, where the second plurality of capsules further comprises a solvent.

20. The system of claim 16, where the material system further is a self-healing material system.

21. The system of claim 16, where the first reactant comprises cyclooctatetraene, and the product comprises poly(acetylene).

22. The system of claim 16, where the metathesis catalyst comprises the Grubbs-Love catalyst.

23. The system of claim 16, where the plurality of particles comprises the metathesis catalyst and an encapsulant.

* * * * *